(12) United States Patent
Osorio

(10) Patent No.: US 11,083,407 B2
(45) Date of Patent: Aug. 10, 2021

(54) PATHOLOGICAL STATE DETECTION USING DYNAMICALLY DETERMINED BODY INDEX RANGE VALUES

(71) Applicant: Flint Hills Scientific, L.L.C., Lawrence, KS (US)

(72) Inventor: Ivan Osorio, Leawood, KS (US)

(73) Assignee: Flint Hills Scientific, LLC, Lawrence, KS (US)

(*) Notice: Subject to any disclaimer, the term of this patent is extended or adjusted under 35 U.S.C. 154(b) by 349 days.

(21) Appl. No.: 14/084,513

(22) Filed: Nov. 19, 2013

(65) Prior Publication Data

US 2014/0275828 A1    Sep. 18, 2014

Related U.S. Application Data

(60) Provisional application No. 61/785,429, filed on Mar. 14, 2013.

(51) Int. Cl.
*A61B 5/0205* (2006.01)
*A61B 5/11* (2006.01)
(Continued)

(52) U.S. Cl.
CPC ............ *A61B 5/4094* (2013.01); *A61B 5/01* (2013.01); *A61B 5/021* (2013.01); *A61B 5/024* (2013.01); *A61B 5/0205* (2013.01); *A61B 5/02055* (2013.01); *A61B 5/1118* (2013.01); *A61B 5/14539* (2013.01); *A61B 5/14542* (2013.01); *A61B 5/14546* (2013.01); *A61B 5/222* (2013.01); *A61B 5/24* (2021.01); *A61B 5/389* (2021.01); *A61B 5/4064* (2013.01); *A61B 5/4266* (2013.01); *A61B 5/7246* (2013.01); *A61B 5/7282* (2013.01); *A61B 5/02405* (2013.01); *A61B 5/0533* (2013.01);
(Continued)

(58) Field of Classification Search
CPC ..................................................... A61B 5/4094
See application file for complete search history.

(56) References Cited

U.S. PATENT DOCUMENTS

| | | | | |
|---|---|---|---|---|
| 2001/0049470 | A1* | 12/2001 | Mault | A61B 5/02055 600/300 |
| 2006/0224067 | A1* | 10/2006 | Giftakis | A61B 5/0402 600/483 |

(Continued)

FOREIGN PATENT DOCUMENTS

| WO | 20070272425 A2 | 6/2007 |
|---|---|---|
| WO | 2011072684 A1 | 6/2011 |

*Primary Examiner* — Niketa I Patel
*Assistant Examiner* — Nathan A Baldwin
(74) *Attorney, Agent, or Firm* — CF3; Stephen Eisenmann

(57) ABSTRACT

We report method of detecting a pathological body state of a patient, comprising receiving a body signal of the patient; determining a body index from said body signal; determining an activity level of said patient; determining a value range for said body index for said patient, based at least in part on said activity level; comparing said body index to said value range; and detecting a pathological state when said body index is outside said value range. We also report a medical device system configured to implement the method. We also report a non-transitory computer readable program storage unit encoded with instructions that, when executed by a computer, perform the method.

22 Claims, 10 Drawing Sheets

(51) Int. Cl.
*A61B 5/00* (2006.01)
*A61B 5/01* (2006.01)
*A61B 5/021* (2006.01)
*A61B 5/145* (2006.01)
*A61B 5/22* (2006.01)
*A61B 5/024* (2006.01)
*A61B 5/24* (2021.01)
*A61B 5/389* (2021.01)
*A61B 5/0533* (2021.01)
*A61N 1/36* (2006.01)

(52) U.S. Cl.
CPC ........... *A61B 5/1123* (2013.01); *A61B 5/7275* (2013.01); *A61N 1/36064* (2013.01); *G01N 2800/2857* (2013.01)

(56) References Cited

U.S. PATENT DOCUMENTS

| | | | |
|---|---|---|---|
| 2008/0188763 A1* | 8/2008 | John | A61B 5/0452 600/516 |
| 2010/0106217 A1* | 4/2010 | Colborn | A61N 1/36082 607/45 |
| 2010/0121215 A1* | 5/2010 | Giftakis et al. | 600/544 |
| 2010/0298656 A1* | 11/2010 | McCombie et al. | 600/301 |
| 2011/0066062 A1* | 3/2011 | Banet | A61B 5/0402 600/534 |
| 2012/0277605 A1* | 11/2012 | Colborn | A61B 5/024 600/508 |
| 2012/0296175 A1 | 11/2012 | Poh et al. | |
| 2013/0116514 A1* | 5/2013 | Kroner | A61B 5/01 600/301 |

\* cited by examiner

PATHOLOGICAL STATE DETECTION USING DYNAMICALLY DETERMINED BODY INDEX RANGE VALUES

FIELD OF THE INVENTION

This disclosure relates to medical device systems and methods capable of detecting a pathological body state of a patient, which may include epileptic seizures, and responding to the same.

SUMMARY OF THE INVENTION

In some embodiments, the present disclosure relates to a method of detecting a pathological body state of a patient, comprising receiving a body signal of the patient; determining a first body index from said body signal; determining an activity level of said patient; determining a non-pathological range for said first body index, based at least in part on said activity level; comparing said first body index to said non-pathological range for said first body index; and detecting a pathological body state when said body index is outside said non-pathological range.

In some embodiments, the present disclosure relates to a method of determining a pathological state in a patient, comprising receiving data relating to an activity level of said patient; determining an activity level of the patient based on said data relating to an activity level; receiving at least one body signal of the patient; determining at least a first body index based on said at least one body signal; dynamically determining a non-pathological range for said at least a first body index based on said activity level; determining that the patient is in one of a non-pathological state and a pathological state, wherein said patient is determined to be in a non-pathological state if the at least a first body index is within said non-pathological range, and said patient is determined to be in a pathological state if the at least a first body index is outside said non-pathological range or is incommensurate for said patient with said activity type and level; and taking at least one further action based on determining that the patient is in a pathological state, wherein said further action is selected from treating said pathological state, issuing a warning to the patient or a caregiver regarding said pathological state, logging the occurrence of said pathological state, or logging a severity of said pathological state.

In other embodiments, the present disclosure relates to a medical device system comprising: at least one kinetic sensor, each said sensor configured to collect at least one kinetic signal from a patient; an activity level module configured to determine an activity level of said patient, based at least in part on said at least one kinetic signal; at least one sensor configured to sense a body signal; a body index determination module configured to determine at least a first body index based on said sensed body signal; a body index range module, configured to determine a non-pathological body index range of said at least a first body index, based at least in part on said activity type and level; and a pathological state determination module, configured to determine that the patient is in one of a non-pathological state and a pathological state, wherein said patient is determined to be in a non-pathological state if the at least a first body index is within said non-pathological body index range for said at least a first body index, and said patient is determined to be in a pathological state if the at least a first body index is outside said non-pathological body index range for said at least a first body index.

In other embodiments, the present disclosure relates to a medical device system, comprising at least one metabolic sensor configured to collect at least one metabolic signal relating to an activity level of said patient; an activity level module configured to determine an activity level of said patient based at least on part on said at least one metabolic signal; at least one sensor configured to sense a body signal; a body index determination module configured to determine at least one body index based on said sensed body signal; a body index range module, configured to determine a non-pathological body index range based at least in part on said activity level; and a module, configured to determine that the patient is in one of a non-pathological state and a pathological state, wherein said patient is determined to be in a non-pathological state if the first body index is within said non-pathological body index range, and said patient is determined to be in a pathological state if the first body index is outside said non-pathological body index range.

In some embodiments, the activity refers to physical activity (e.g., body movements), while in other embodiments, activity refers to cerebral activity (e.g., cognitive, emotional or other brain activity).

In some embodiments, the present disclosure relates to a non-transitory computer readable program storage unit encoded with instructions that, when executed by a computer, perform a method as described above.

BRIEF DESCRIPTION OF THE DRAWINGS

The disclosure may be understood by reference to the following description taken in conjunction with the accompanying drawings, in which like reference numerals identify like elements, and in which.

Figure 1:
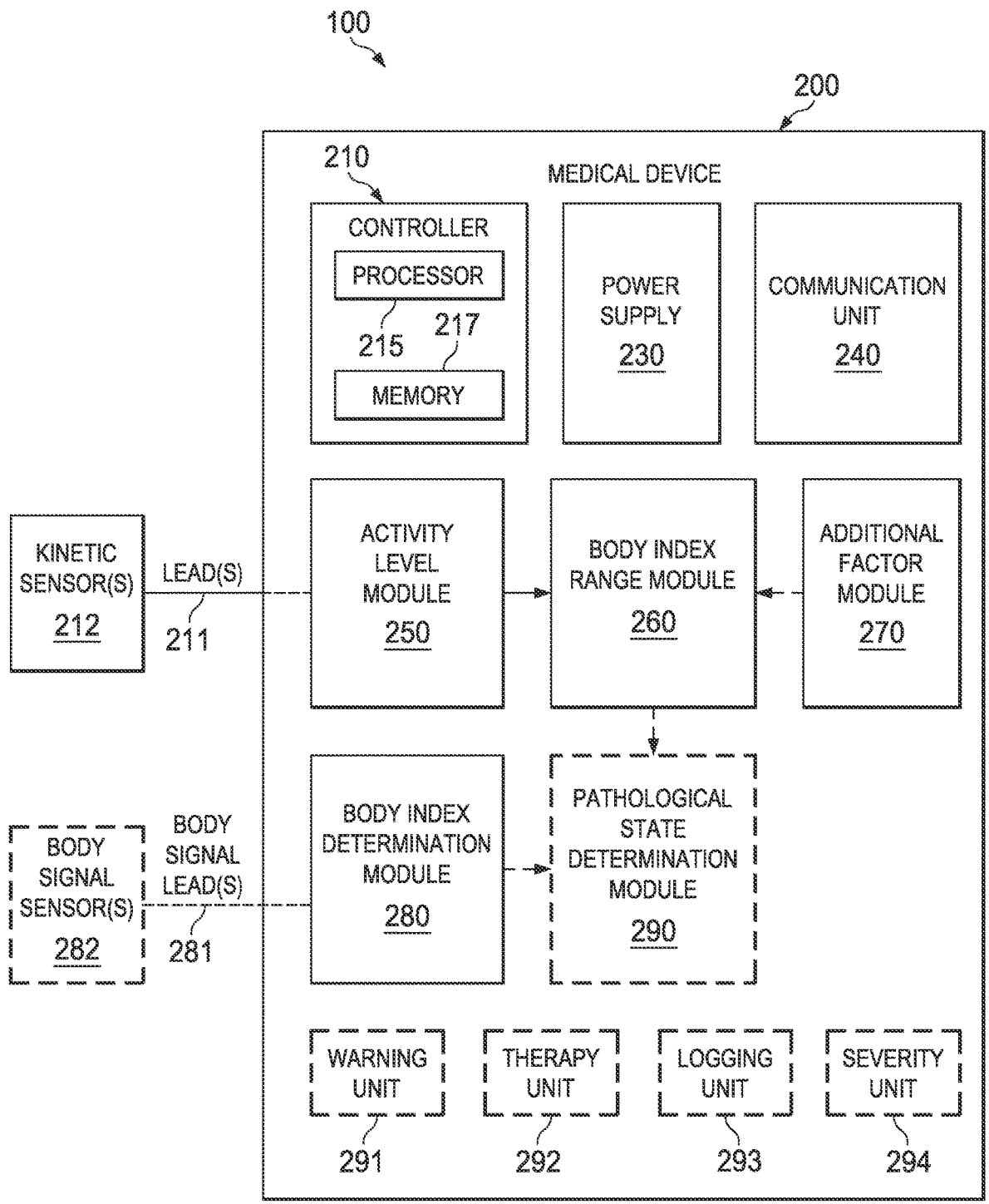
FIG. 1 shows a schematic representation of a medical device system, according to some embodiments of the present disclosure.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION OF SPECIFIC EMBODIMENTS

Illustrative embodiments of the disclosure are described herein. For clarity, not all features of an actual implementation are described. In the development of any actual embodiment, numerous implementation-specific decisions must be made to achieve design-specific goals, which will vary from one implementation to another. Such a development effort, while possibly complex and time-consuming, would nevertheless be a routine undertaking for persons of ordinary skill in the art having the benefit of this disclosure.

Embodiments of the present disclosure provide for a medical device capable of monitoring an activity type and/or level of a patient and dynamically determining a non-pathological body index range based upon an activity type and/or level of the patient. The dynamically determined body index range may be used to classify a body system of the patient as being in a pathological or non-pathological state. An activity level of the patient may in some embodiments be determined from a kinetic sensor such as an accelerometer, while in other embodiments activity level may refer to a metabolic activity level as determined from a metabolic sensor measuring, e.g., glucose consumption or blood pH or oxygen consumption. Kinetic sensors for use in embodiments herein may include any sensor that measures a kinetic activity of the patient, including movement, acceleration, velocity, position, force, or direction plus duration. The classification of body systems of the patient as pathological or non-pathological may further be based on health status, fitness level and prevailing environmental conditions (e.g., temperature, altitude, humidity, time of day, etc.) or patient characteristics (e.g., age, gender, BMI, fitness level, medications).

This invention recognizes that to determine (using body systems and their features) whether a body system is functioning pathologically or non-pathologically with a clinically worthwhile degree of accuracy and reliability, one must take into account the type and/or level of activity being performed by a subject at the time the pathological/non-pathological determination is made. For example, if the objective is to determine if and when a patient is in a seizure state that manifests with increases in heart rate, it is imperative to know whether or not a given increase in heart rate is associated with a change in activity (e.g., physical or emotional) and if such a change in activity is occurring, to determine if the heart rate increase is commensurate with said activity type and level. This may be accomplished by a dynamical adjustment of value ranges of body signal features to avoid false diagnoses.

In some embodiments, a non-pathological range for a body index may be dynamically determined (which may include an adjustment to a previously determined non-pathological body index range) based on the activity type and/or level of the patient. As used herein, the determination or adjustment may be considered to be "based on" the activity level so long as the determination of the non-pathological range takes into consideration the activity level, even though other factors (e.g., patient-specific or patient environmental factors) may also be used to determine the non-pathological range. In some embodiments, more than one body index from at least one body signal may be determined, and corresponding non-pathological ranges for each of the body indices may be determined based on the activity type and/or level. Once the non-pathological body range is determined, a determination of a pathological or a non-pathological state of the patient may be made by comparing the body index to the dynamically determined non-pathological body index range. In particular, the patient may be determined to be in a non-pathological state if the body index is within the non-pathological body index range, and the patient may be determined to be in a pathological state if the first body index is outside the non-pathological body index range. Where multiple body indices and corresponding non-pathological body ranges are determined, the determination of a pathological or non-pathological state may be based on more than one such index and range. When a detection of a pathological state is made, the medical device may perform a responsive action, such as providing a therapy, providing a warning, determining a severity of the pathological state, and/or logging the determination of the pathological state. FIG. 1 shows a schematic representation of a medical device system, according to some embodiments of the present disclosure. The medical device system 100 may comprise a medical device 200, kinetic sensor(s) 212, lead(s) 211 coupling the kinetic sensor(s) 212 to the medical device 200, body signal sensors 282 and body signal leads 281 coupling body signal sensors 282 to medical device 200. The medical device system 100 may be fully or partially implanted, or alternatively may be fully external. In one embodiment, kinetic sensor(s) 212 may each be configured to collect at least one signal from a patient relating to an activity level of the patient. For example, each kinetic sensor 212 may be selected from an accelerometer, an inclinometer, a gyroscope, an ergometer, an electromyography (EMG) sensor, a body temperature sensor, an oxygen consumption sensor, a lactic acid accumulation sensor, a sweat sensor, a neurogram sensor, a force transducer, or an ergometer. Brain, metabolic or other sensors may be used in some embodiments. For example sensors (electrical, thermal, chemical, etc.) may be placed in one more structures (cortex, basal ganglia, cortico-spinal tract, cerebellum) involved in motor control to determine the physical work performed by a person.

Various components of the medical device 200, such as controller 210, processor 215, memory 217, power supply 230, communication unit 240, warning unit 291, therapy unit 292, and logging unit 293 and severity unit 294 have been described in other patent applications assigned to Flint Hills Scientific, LLC or Cyberonics, Inc., such as, U.S. Ser. No. 12/770,562, filed Apr. 29, 2010; U.S. Ser. No. 12/771,727, filed Apr. 30, 2010; U.S. Ser. No. 12/771,783, filed Apr. 30, 2010; U.S. Ser. No. 12/884,051, filed Sep. 16, 2010; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598,339, filed Aug. 29, 2012; U.S. Ser. No. 12/896,525, filed Oct. 1, 2010, now U.S. Pat. No. 8,337,404, issued Dec. 25, 2012; U.S. Ser. No. 13/098,262, filed Apr. 29, 2011; U.S. Ser. No. 13/288,886, filed Nov. 3, 2011; U.S. Ser. No. 13/554,367, filed Jul. 20, 2012; U.S. Ser. No. 13/554,694, filed Jul. 20, 2012; U.S. Ser.

No. 13/559,116, filed Jul. 26, 2012; and U.S. Ser. No. 13/598,339, filed Aug. 29, 2012. Each of the patent applications identified in this paragraph is hereby incorporated herein by reference.

The medical device 200 may comprise an activity level module 250, configured to determine an activity type and/or level of the patient, based at least in part on body signal data collected by sensor(s) 212. By "activity level" is meant the level of one or more of the patient's energy consumption (which may be termed "work level" and may conveniently be measured by proxies such as body movement, EMG activity, $O_2$ consumption or heart rate, among others, and from which the classical definition of work is not excluded), emotional activity (e.g., mild versus intense emotion), or cognitive activity (e.g., mild versus intense thinking) In some embodiments, information relating to work level may be collected by an accelerometer, etc. described above.

The activity level module 250 may determine an activity level of the patient at any sampling frequency for kinetic sensors 212. In one embodiment, the activity level module 250 is configured to determine the activity level with a sampling frequency ranging from about one thousand times per second to about once every four hours. The activity level module 250 may determine an activity level for at least one time window or may determine an instantaneous measure of activity. The at least one time window may be on a microscopic time scale (less than 10 min), a mesoscopic timescale (10 min-24 hr), or a macroscopic timescale (greater than 24 hr). Other temporal scales (smaller or larger) than those listed above may be applied. The medical device 200 may also comprise a body index range module 260, configured to determine body index ranges of the patient, based at least in part on the activity level determined by the activity level module 250. In some embodiments, the body index range module 260 may determine a reference value range for a certain body index (e.g., heart rate). In one embodiment, the body index range module 260 may determine a non-pathological range for a particular body index based on the activity level determined by the activity level module 250. By comparing an actual body index (e.g., as determined from a body index by a body index determination module 280) to the reference value range (e.g., a non-pathological range), it is possible to determine whether the actual body index is in the non-pathological range or in a pathological range. Because of variations in pathological and non-pathological ranges associated with activity levels, a particular actual body index value may indicate that the patient is in a pathological state at one activity level but indicate that the patient is in a non-pathological state at another activity level. Thus, body index range module 260 may determine that the same body index value (e.g., the same heart rate) in the same patient is either pathological or non-pathological based on the activity level, activity type, or other variables (e.g., fitness level). In some embodiments, the body index range module 260 may determine both a pathological range value and a non-pathological range value for the one or more body indices. By taking into account the effects on body indices of activity levels (e g, kinetic activity or metabolic activity), non-pathological ranges for particular indices derived from monitored body signals may be dynamically determined (which includes dynamic adjustment of the indices) so that detection of pathological states may be made with great accuracy. That is, false negative and false positive detections of pathological events may be reduced by dynamically determining pathological or non-pathological ranges for particular body indices based on activity type and level or other variables (e.g., environmental conditions).

In some embodiments, ranges determined by the body index range module 260 may be based upon additional factors beside the activity level of the patient. For example, determination of a reference value range (e.g., a non-pathological body index range or a pathological body index range) may, in addition to the activity level of the patient, be based on data collected in real-time, and may include patient body data and/or environmental conditions that have an influence on the non-pathological body index ranges. These actions may be performed with or without regard to the patient's body systems' status (normal or abnormal), and adjustments may be made to the boundaries of the non-pathological (or pathological) range so that a real-time body index value may, in certain situations or circumstances, be indicative of a certain pathological state (e.g., epileptic seizure) and in others, not be indicative of the pathological state. In an adult with a resting heart rate of 110 bpm (indicative of cardiac dysfunction) who also suffers from epilepsy, seizures may further elevate the heart rate and said elevation in the context of no change in activity type or level, would be indicative of the occurrence of an epileptic seizure in said subject. That is, the collected body data may be a priori, normal or abnormal and if abnormal, the occurrence of a transient/reversible change in the state of a body system may further alter said abnormal activity.

In such embodiments, the additional factor(s) may be determined by an additional factor module 270 configured to determine one or more of a time of day, an environmental condition, a patient's body weight and height, a patient's body mass index, a patient's gender, a patient's age, an indicator of said patient's overall health, or an indicator of said patient's overall fitness, and provide an output relating to the additional factor determination. The body index range module 260 may then be configured to determine a non-pathological body index range based at least in part on the output of the additional factor module 270.

The body index range module 260 may be configured to determine said reference value range (e.g., non-pathological or pathological body index range) based at least in part on a kinetic signal collected from a time window ending at the current time. In some embodiments, the body index range module 260 may perform calculations based upon a moving time window used to collect body signals.

In one embodiment, the body index range module 260 may be configured to determine a non-pathological range for a first time point based on the patient's activity in a first time window prior to said first time point. The first time window may comprise a time interval ranging from 1 second to two hours. In one embodiment, the first time window may comprise one of: said first time point and the preceding 1 second; said first time point and the preceding 10 seconds; said first time point and the preceding 30 second; said first time point and the preceding 1 minute; said first time point and the preceding 2 minutes; said first time point and the preceding 3 minutes; said first time point and the preceding 5 minutes; said first time point and the preceding 10 minutes; said first time point and the preceding 30 minutes; said first time point and the preceding 1 hour; said first time point and the preceding 2 hours. In some embodiments, the body index range module 260 may also use the patient's historical health information to generate a non-pathological range for one or more body indices. Historical data of the patient may provide indications as to expected changes in nonpathological ranges of the body index during certain time periods.

The body index range module 260 may make its determination at any sampling frequency. In one embodiment, the body index range module 260 is configured to configure to determine a non-pathological body index range for a body index (e.g., an instantaneous or average heart rate) at an update frequency ranging from about one thousand times per second to about once every four hours.

The medical device 200 may further comprise a body index determination module 280, configured to determine one or body indices of the patient. The body index may be heart rate (instantaneous or in a short-term or long-term time window), heart rate rhythm, heart rate variability, blood pressure, blood pressure variability, respiratory rate, respiratory rhythm, respiratory rate variability, end tidal $CO_2$, kinetic activity, cognitive activity, dermal (including electrodermal) activity, chemical (including electro-chemical) activity, arterial pH, cortisol level, catecholamine level, or blood oxygen saturation, among others. For example, the body index may be heart rate. The body index may be determined based on a signal collected from one or more body signal sensor(s) 282, which may be coupled to the medical device 200 by body signal lead(s) 281.

The medical device 200 may further comprise a pathological state determination module 290, configured to determine an occurrence of a pathological state of the patient, in response to the body index being outside of a non-pathological or a pathological body index range for the body index for the prevailing activity type, level and other conditions. An occurrence of any pathological state that may be associated with a body signal outside a non-pathological body index range provided by analysis of the patient's activity level may be determined by the pathological state occurrence module 290.

In one embodiment, the pathological state is an epileptic event, e.g., an epileptic seizure. For example, if the body signal is heart rate, then an instantaneous heart rate above the non-pathological heart rate range determined by the body index range module 260 may indicate a tachycardia episode frequently seen with epileptic seizures originating from or spreading to certain brain regions, and an instantaneous heart rate below the non-pathological heart rate range may indicate a bradycardia episode occasionally seen with epileptic seizures originating from certain brain regions. By taking into account the activity level of the patient and other conditions, false positive and/or negative detections of pathological events may be avoided, since the effects of high or low activity levels upon heart rate may be used to adjust (e.g., raise, lower, widen or narrow) non-pathological or pathological heart rate ranges. For example, if the patient is engaged in vigorous exercise, the non-pathological range for heart rate may be increased and the range may be widened. If the patient is sedentary or sleeping, acceptable non-pathological ranges for heart rate may be lowered and narrowed.

Figure 2A:
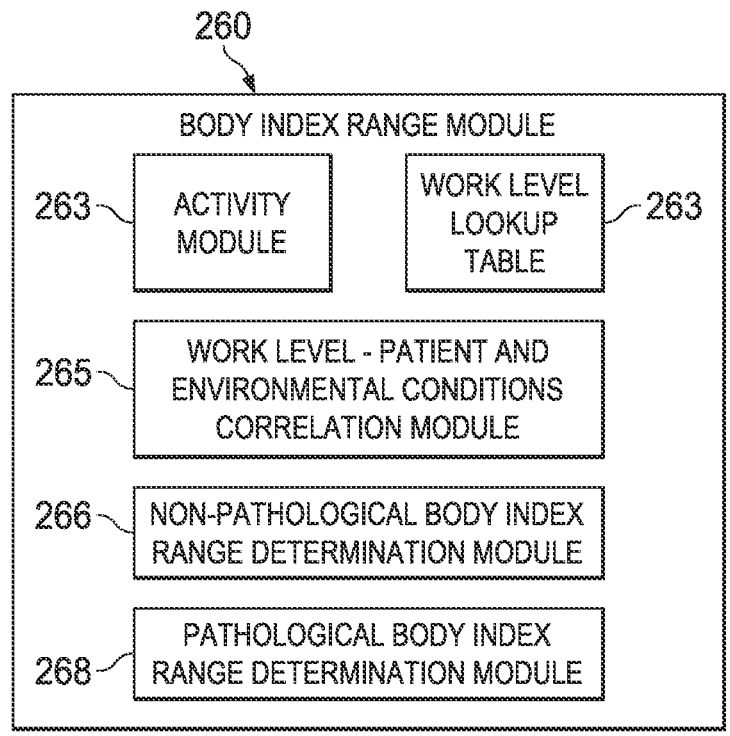
FIG. 2A shows a schematic representation of a body index range module of the medical device system of FIG. 1, according to some embodiments of the present disclosure.

FIG. 2A shows a block diagram schematic representation of the body index range module 260 in more detail, according to some embodiments of the present disclosure. The body index range module 260 may comprise an activity module 263. The activity module 263 may be configured to provide a determination of the source(s) of the patient's activity level, e.g., whether the sources are kinetic (body movement), emotional, or cognitive activity.

The body index range module 260 may comprise a work level lookup table 264. The work level lookup table 264 may provide information relating a non-pathological body index range to an activity level of the patient. In one embodiment, the work level may refer to the metabolic changes in the patient's body based upon the amount of energy expended by the patient. However, other measures of work level may be also used, including the classic reference to work level involving amount of force used, displacement, etc. For example, if the body index is heart rate, an activity level indicative of vigorous aerobic exercise may be related to a non-pathological heart rate range of 120-140 BPM.

The body index range module 260 may comprise a work level—patient and environmental conditions correlation module 265. The work level—patient and environmental conditions correlation module 265 may perform a correlation of information from the additional factor module 271 and the work level lookup table 264 to determine a non-pathological body index range from the current patient and environmental conditions and current work level and source(s) thereof.

The body index range module 260 may further comprise a non-pathological body index range determination module 266. The non-pathological body index range determination module 266 may determine the non-pathological body index range from the patient's activity level for a given work level as determined by one or more of activity module 263, work level lookup table 264, or work level—patient and environmental conditions module 265. In some embodiments, the body index range module 260 may further comprise a pathological body index range determination module 268, which may determine a pathological body index range from by one or more of activity module 263, work level lookup table 264, or work level—patient and environmental conditions module 265.

Figure 2B:
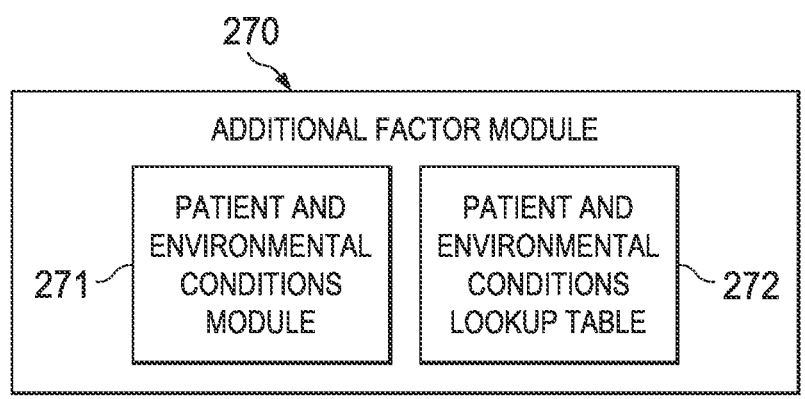
FIG. 2B shows a schematic representation of an additional factor module of the medical device system of FIG. 1, according to some embodiments of the present disclosure.

FIG. 2B shows a block diagram schematic representation of the additional factor module 270 in more detail, according to some embodiments of the present disclosure. Additional factor module 270 may comprise a patient and environmental conditions module 271. The patient and environmental conditions module 271 may be configured to provide a determination of one or more patient and environmental conditions. For example, the patient and environmental conditions module 271 may be configured to provide the time of day, such as by maintaining an internal clock, fetching a clock value from the processor 210, or requesting a time of day value from an external source via communication unit 240, among others. For another example, the patient and environmental conditions module 271 may be configured to provide the ambient temperature or the ambient humidity, altitude, such as by requesting the temperature from a thermometer, or the humidity from a hygrometer, in contact with ambient air. For additional examples, the patient and environmental conditions module 271 may be configured to provide the patient's body weight, the patient's BMI, or the patient's fitness level, among other factors.

The additional factor module 270 may comprise a patient and environmental conditions lookup table 272. The patient and environmental conditions lookup table 272 may provide information relating a non-pathological or pathological body index range to patient and environmental conditions as determined by module 271. For example, if the body index is heart rate, and the environmental condition is the time of day, a time of day between midnight and 6:00 AM may be related to a non-pathological heart rate range of 40-70 BPM, and this relation may be stored in patient and environmental conditions lookup table 272.

Figure 3A:
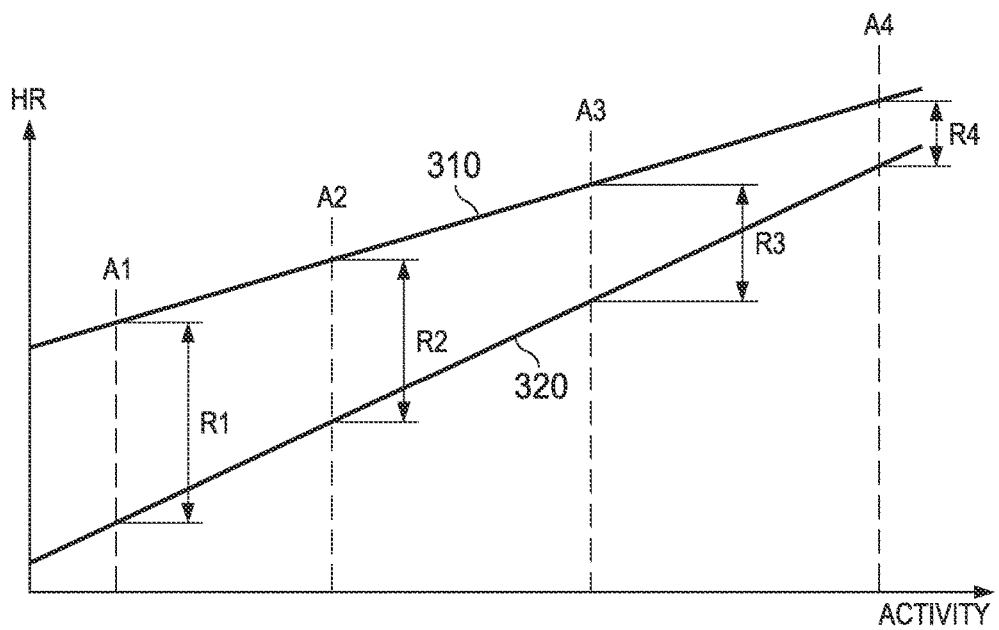
FIG. 3A shows the dynamic nature of an exemplary non-pathological heart rate range, according to some embodiments of the present disclosure.

FIG. 3A shows the dynamic relationship between non-pathological patient activity levels (e.g., as determined from a tri-axial accelerometer) and an exemplary body index (heart rate). The patient's activity level is shown on the x-axis and heart rate (HR) is on the y-axis. Although non-pathological activity level is shown in FIG. 3A as a single continuous parameter, a plurality of discrete activity levels or states may also be used to correlate heart rate (or another body index) to activity levels in some embodiments of the invention. Because heart rate is a non-stationary parameter that may be influenced by many different factors in addition to activity levels (e.g., the patient's age, sex, body mass index, fitness level, hydration status, environmental conditions such as temperature, humidity, etc.) a particular activity level may result in a short-term heart rate anywhere within the associated non-pathological heart rate range.

FIG. 3A shows an activity-based, non-pathological heart rate range region bounded by upper non-pathological HR boundary line 310 and lower non-pathological HR boundary line 320. Both the upper and lower bounds of the non-ictal heart rate region increase as activity level increases (e.g. from a sleep state to a resting, awake state) and reach their highest values for strenuous exertion. In addition, the width of the non-pathological heart rate ranges narrows as activity levels and heart rates increase, which is consistent with the known reduction in heart rate variability at high levels of exertion. When the patient is in a non-pathological state (e.g., when an epileptic patient is not having a seizure), for a particular activity level the patient's short-term heart rate should fall within a non-pathological heart rate range associated with that activity level. Referring to FIG. 3A, at a particular activity level A1—corresponding to a sleeping activity level—a non-pathological HR range R1 may be determined between upper and lower boundaries 310 and 320. Another non-pathological heart rate range R2 may be established by upper and lower boundaries 310 and 320 for resting awake activity level A2. At activity levels A3 and A4, corresponding to moderate and strenuous exercise, respectively, corresponding non-pathological HR ranges R3 and R4 may be determined from upper boundary 310 and lower boundary 320. As noted, the width of the non-pathological heart rate ranges decrease as activity levels increase, and thus R1>R2>R3>R4.

Figure 3B:
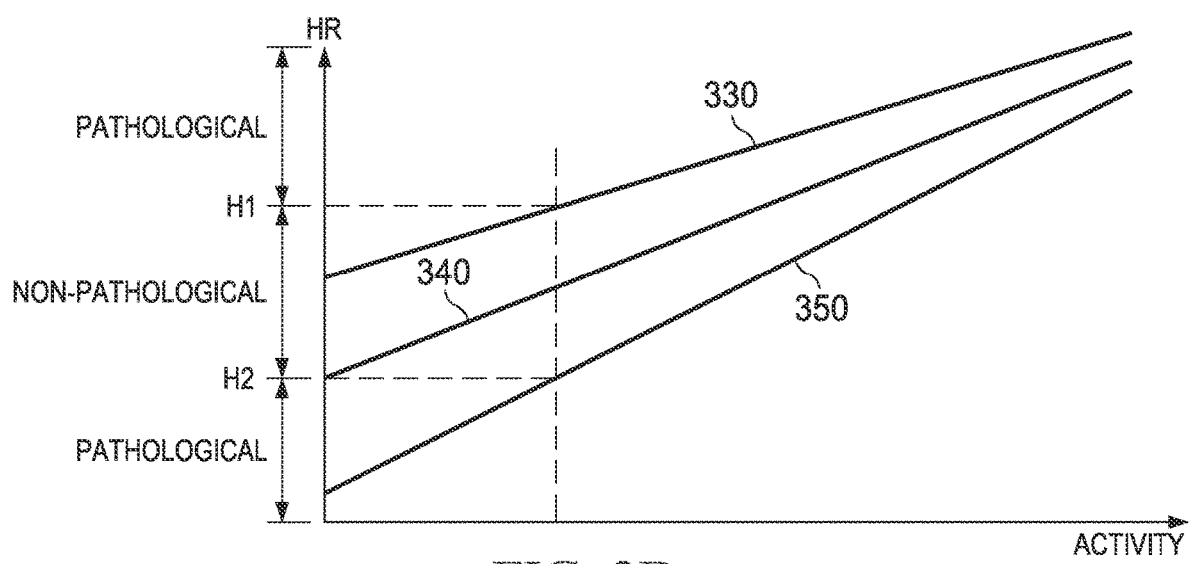
FIG. 3B shows the dynamic nature of an exemplary non-pathological heart rate range, according to some embodiments of the present disclosure.

Referring to FIG. 3B, non-pathological heart rate ranges as a function of activity level are determined by upper and lower boundaries 330, 350. For a particular activity level A5, the non-pathological range lies between heart rate H1 and H2. At heart rates above H1, the patient's heart rate may be pathologically high (e.g., when the patient is having a seizure characterized by elevated heart rate), while at heart rates below H2, the patient's heart rate may be pathologically low (e.g., when the patient is having a seizure characterized by reduced heart rate).

Upper and lower non-pathological heart rate boundaries 330, 350 may be determined from patient population data and stored in a memory of an implantable or body-worn medical device. When needed, the heart rate data may be retrieved from the memory for use by the medical device to determine whether the patient's heart rate is within a non-pathological range appropriate in view of the patient's activity level. Alternatively, heart rate ranges may be determined by calculation from a formula based on the patient's activity level, which may optionally take into account one or more additional factors such as those previously mentioned.

Upper and lower boundaries 330, 350 may alternatively be determined empirically from patient-specific data collected over time for a variety of activity levels. For example, the patient may be subjected to one or more stress tests such as a walking test on a treadmill, with heart rates determined at each of a variety of different activity levels (e.g., as determined from one or more of a three-dimensional accelerometer, an electromyogram, gyroscope, and/or imaging devices such as a camera). Other activity level tests may be performed to determine upper and lower boundaries 330, 350. In one embodiment, upper non-pathological boundary 330 may be determined as an upper percentile value (e.g., the $90^{th}$, $95^{th}$, or $99^{th}$ percentile) of the non-pathological heart rates measured at times corresponding to the particular activity level. Thus, a linear or higher-order polynomial may be fitted through the target upper percentile values over a range of activity levels to obtain the upper boundary 330. Similarly, another polynomial may be fitted through a target percentile value (e.g., $5^{th}$, $2^{nd}$, $1^{st}$) to obtain the lower boundary 350.

Additional curves may be determined by fitting polynomials to additional target percentile values of the activity level/HR data. Referring again to FIG. 3B, a median boundary line 340 may be determined by fitting a polynomial through the $50^{th}$ percentile values over the range of activity levels. Additional percentile values may be determined similarly. In addition, the overall range may be further divided into sub-ranges (e.g., first, second, third and fourth quartile ranges).

In some embodiments of the present invention, upper and lower boundaries may be determined for one or more specific types of pathological states. For example, separate upper and lower heart rate boundaries as a function of activity level may be determined for simple partial seizures, complex partial seizures, or generalized tonic-clonic seizures, among others. Without being bound by theory, these upper and lower boundaries for each seizure type may be determined as specific percentile value curves from those described immediately above. For example, in one embodiment a non-pathological boundary for a simple partial seizure may be determined as a $90^{th}$ percentile value for a particular activity level, while a non-pathological boundary for a complex partial seizure may be determined as a $95^{th}$ percentile value for a particular activity level.

In some embodiments, upper and lower boundaries for simple partial and complex partial seizures may be determined by activity levels and the results of an awareness test. Where the awareness test indicates that the patient has not lost awareness, the heart rates measured while the patient remains aware may be used (along with activity levels) as data to determine upper and lower heart rate boundaries for simple partial seizures. When and if the patient loses awareness, the data of heart rate and activity level may be used to determine upper and lower activity level heart rate boundaries for seizures associated with loss of function, such as complex partial, complex partial with secondary generalization, or generalized seizures.

FIG. 3A and FIG. 3B together show that a non-pathological heart rate (or other body index) range may be established for a given activity level of the patient. In some embodiments, the range may be a unique range based on historical data for the patient, while in other embodiments data for patient populations may be used, at least until patient-specific data can be obtained. For simplicity, FIG. 3A and FIG. 3B depict the upper and lower boundaries as being linear. It will be appreciated, however, that the boundaries for an actual patient would not necessarily be linear, particularly where additional factors may be considered.

Figure 4:
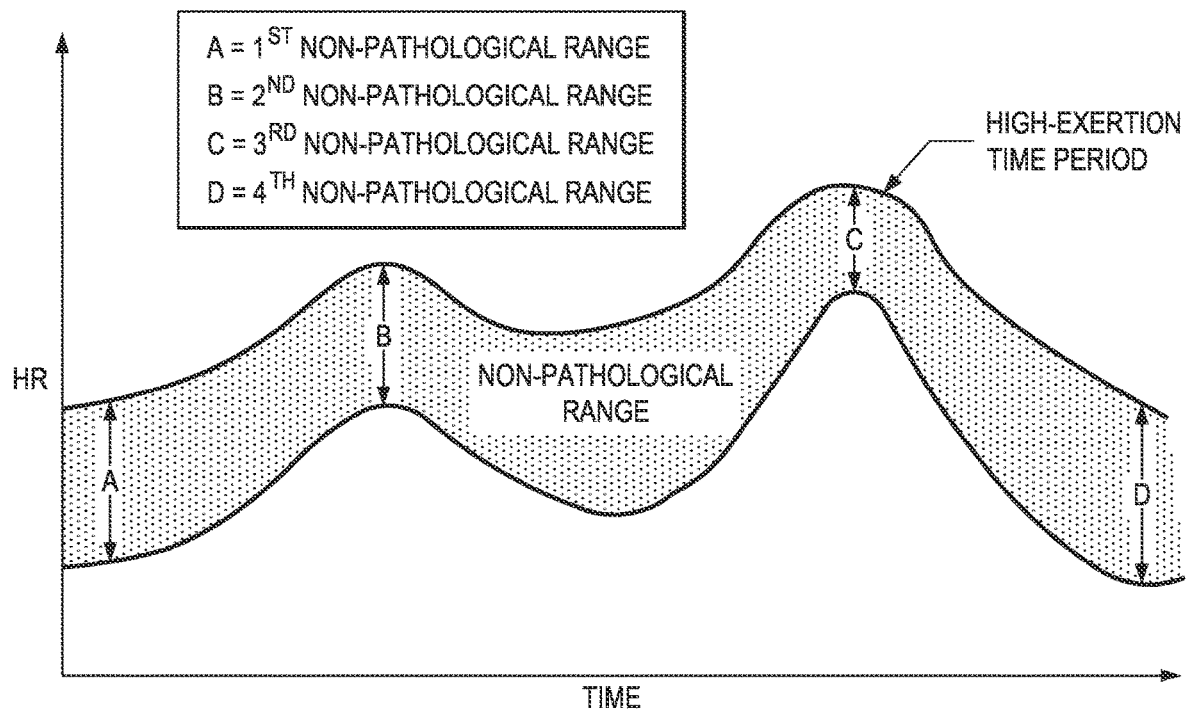
FIG. 4 shows the dynamic nature of an exemplary non-pathological heart rate range in more detail, according to some embodiments of the present disclosure.

The dynamic relationship between non-pathological heart rates and activity levels may be exploited to detect pathological states such as epileptic seizures by determining when the patient's heart rate is incommensurate with the patient's activity level. By monitoring the patient's activity level and heart rate, it is possible to determine when the patient's heart rate falls outside the non-pathological ranges as the patient's activity levels change over time. FIG. 4 shows the patient's heart rate and the dynamically changing non-pathological heart rate range as the patient's activity levels change over time, with time shown on the x-axis and heart rate (HR) and non-pathological heart rate range shown on the Y-axis. As patient activity levels change over the course of time (e.g., over the course of a day), commensurate non-pathological HR ranges may be determined and utilized to detect the onset of pathological states. A non-pathological range A provides a relatively low range that may correspond to sleeping or resting. A slightly higher (and narrower) range B may correspond to higher activity levels of the patient, and a significantly higher (but narrower still) range C may correspond to an exercise period, which returns to a lower (and broader) range D after the patient stops exercising.

Figure 5:
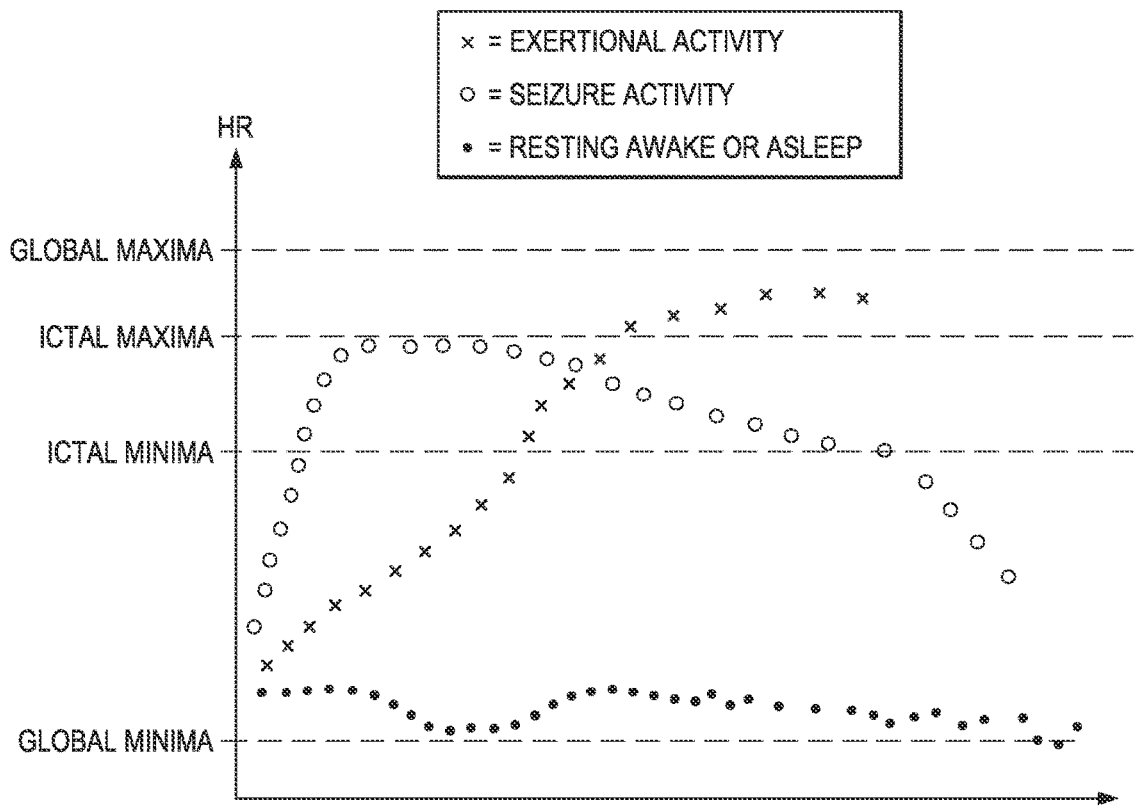
FIG. 5 shows the dynamic nature of an exemplary non-pathological heart rate range in more detail, according to some embodiments of the present disclosure.

FIG. 4 indicates that the width of a non-pathological body index range may change based on activity levels, optionally in view of additional factors as discussed above. For example, at points A and D, the range may relatively broad, reflecting relatively low activity levels. In contrast, at point C, corresponding to strenuous exercise, the range may be relatively narrow, arising from the patient's heart rate approaching his or her maximum heart rate. Periods of elevated heart rate due to exertion may be highly correlated with activity level as measured by, e.g., an accelerometer. FIG. 5 shows the dynamic nature of heart rate changes, along with exemplary thresholds for the global maxima 550, global minima 560, ictal maxima 570 and ictal minima 580 for a particular patient. Heart rate changes associated with an exertional activity are shown by line 530, and for a cycle of waking and sleeping by line 540. During the exertional activity 530, which may occur over a time range from 5 minutes to an hour, the patient's heart rate rises from a non-exertional waking level W to global maxima 550 corresponding the patient's maximum heart rate, and then returns to a baseline non-exertional heart rate W. Global maximum 550 may be reached, for example, during an extended period of vigorous/strenuous exertion or during pathological states. By comparison, a relatively sedentary cycle 540 may take place over a longer time frame, e.g., 1-2 days, and may show a much narrower heart rate ranging from the global minima 560 to waking non-exertional rate W.

FIG. 5 also shows that the exertional heart rate may reach (or exceed) ictal minima 550 and ictal maxima 560 heart rates corresponding to minimum and maximum heart rate values associated with seizures. Thus, FIG. 3A, FIG. 3B, and FIG. 5 show that heart rate alone is insufficient to accurately distinguish pathological and non-pathological states, at least for some activity levels. For lower activity levels, however, the expected heart rate values shown in line 540 may be sufficient to distinguish seizures from non-seizures, if the lower activity level is considered. Thus, for a low activity level as represented by line 540, an expected non-pathological range may be bounded on the low side by the global minima 560, and on the upper side by a rate slightly higher than normal waking rate W, e.g., W+10 bpm. The upper and lower boundaries may vary based on the activity level. Thus, as activity levels rise, both the upper and lower levels of the expected range may be elevated as a function of the activity level and possibly other factors such as the patient's fitness level, age, sex, etc. The less the difference between the ictal minima 550 and the global minima 560, the lower the specificity of detection and the higher the number of false positives. As the activity level increases such that the upper boundary nears the ictal maxima and minima range, the accuracy of distinguishing seizures from non-seizure states may be further diminished if heart rate and activity type/level are the only variables used for pathological state detection purposes. However, by considering additional factors such as the patient's fitness level, age, environmental conditions, etc., accuracy levels may be maintained until activity levels result in body index/indices changes that lie within the range bounded by ictal maxima 570 and ictal minima 580. The degree of overlap between physiological exertional and either pathological exertional or non-exertional (e.g. central neurogenic) changes in body index values is largely dependent on the body index. For example, while heart change increases between a complex partial seizure and a certain exercise activity may be indistinguishable, arterial pH and gases are much less susceptible to changes under physiologic conditions and therefore more specific indicators (than heart rate) of the onset of pathological states.

Although FIG. 3A-5 are directed to heart rate and a non-ictal range, analogous non-pathological ranges may be determined for heart rate variability, blood pressure, respiratory rate, dermal activity, or oxygen saturation, among others. As with heart rate, such other body indices may also be expected to vary with time of day, activity level, or other parameters. Also, disorders other than epilepsy would be expected to have non-pathological ranges of one or more of these body indices.

Figure 6:
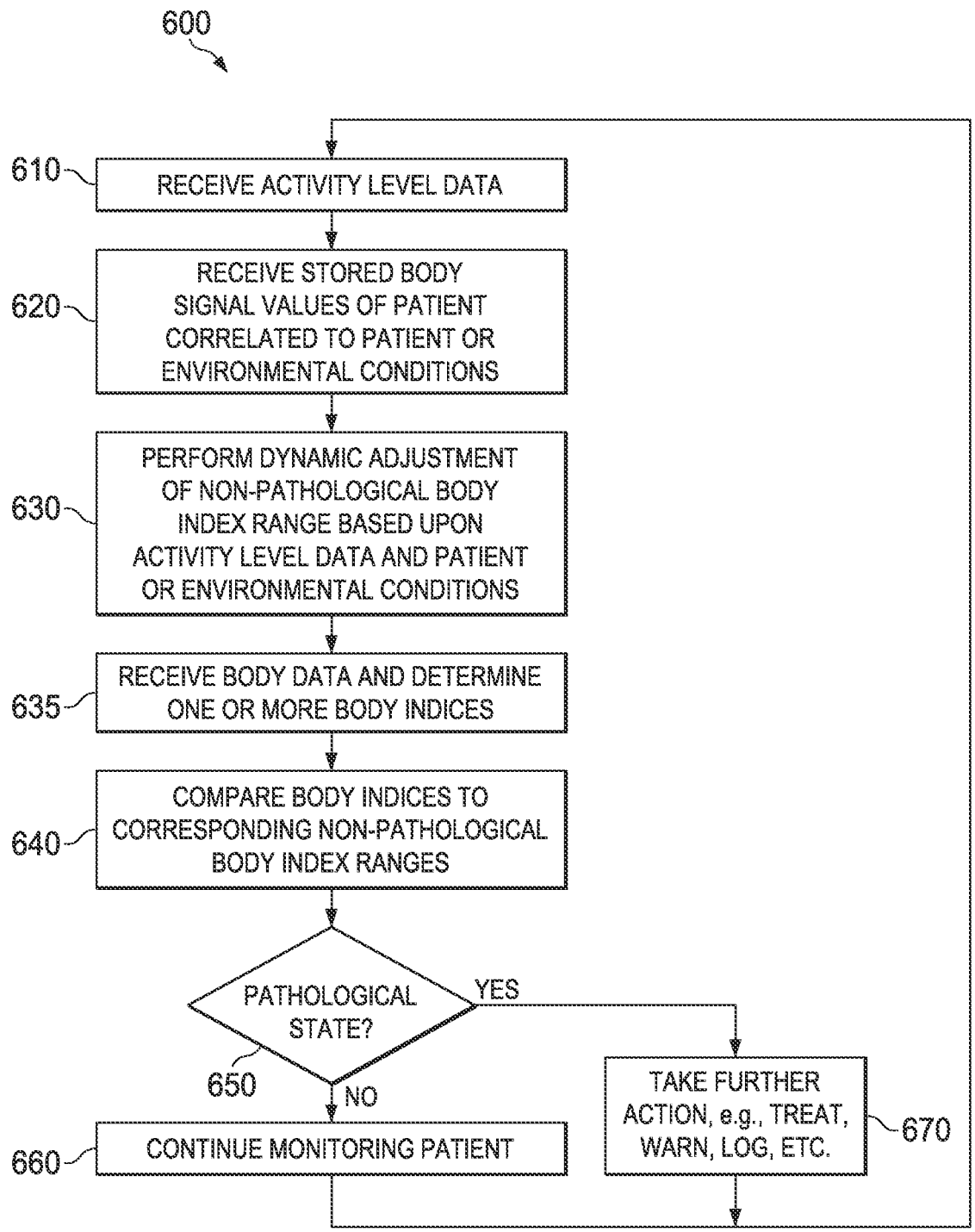
FIG. 6 shows a flowchart representation of a method, according to some embodiments of the present disclosure.

FIG. 6 shows a flowchart representation of a method 600, according to some embodiments of the present disclosure. The method 600 may comprise receiving activity level data at 610. The method 600 may, in some embodiments, also comprise receiving at 620 data related to one or more patient or environmental conditions.

The method 600 may comprise dynamically adjusting at 630 a non-pathological body index range based upon at least on activity level data, and optionally based on the patient or environmental conditions. In some embodiments, the non-pathological body index range may be adjusted by updating either or both of the lower or upper bounds of the range, or selecting the range from a lookup table or bank of ranges.

The method also comprises receiving body data and determining one or more body indices at 635. The one or more body indices correspond to the indices for which non-pathological (or pathological) ranges have been determined at 630. The body indices may be compared at 640 to the dynamically adjusted non-pathological (or pathological) body index ranges. If the patient is found at 650 to be in a pathological state, e.g., if the patient's body index is outside the non-pathological body index range (or if the reference pathological values are incommensurate for the activity type, level and/or other conditions), the method 600 may comprise at least one further action taken at 670, e.g., treating the pathological state, issuing a warning to the patient or a caregiver regarding the pathological state, logging the occurrence and/or the severity of the pathological state, etc. In one embodiment, the severity may be measured by a magnitude and/or duration of a pathological state such as a seizure, a type of autonomic change associated with the pathological state (e.g., changes in heart rate, breathing rate, brain electrical activity, the emergence of one or more cardiac arrhythmias, etc.). If the patient is found at 650 to not be in a pathological state, the method 600 may comprise continued monitoring of the patient at 660. In either event, after the further action(s) taken at 670 or the continued monitoring at 660, flow may return to receiving activity level data at 610.

Figure 7:
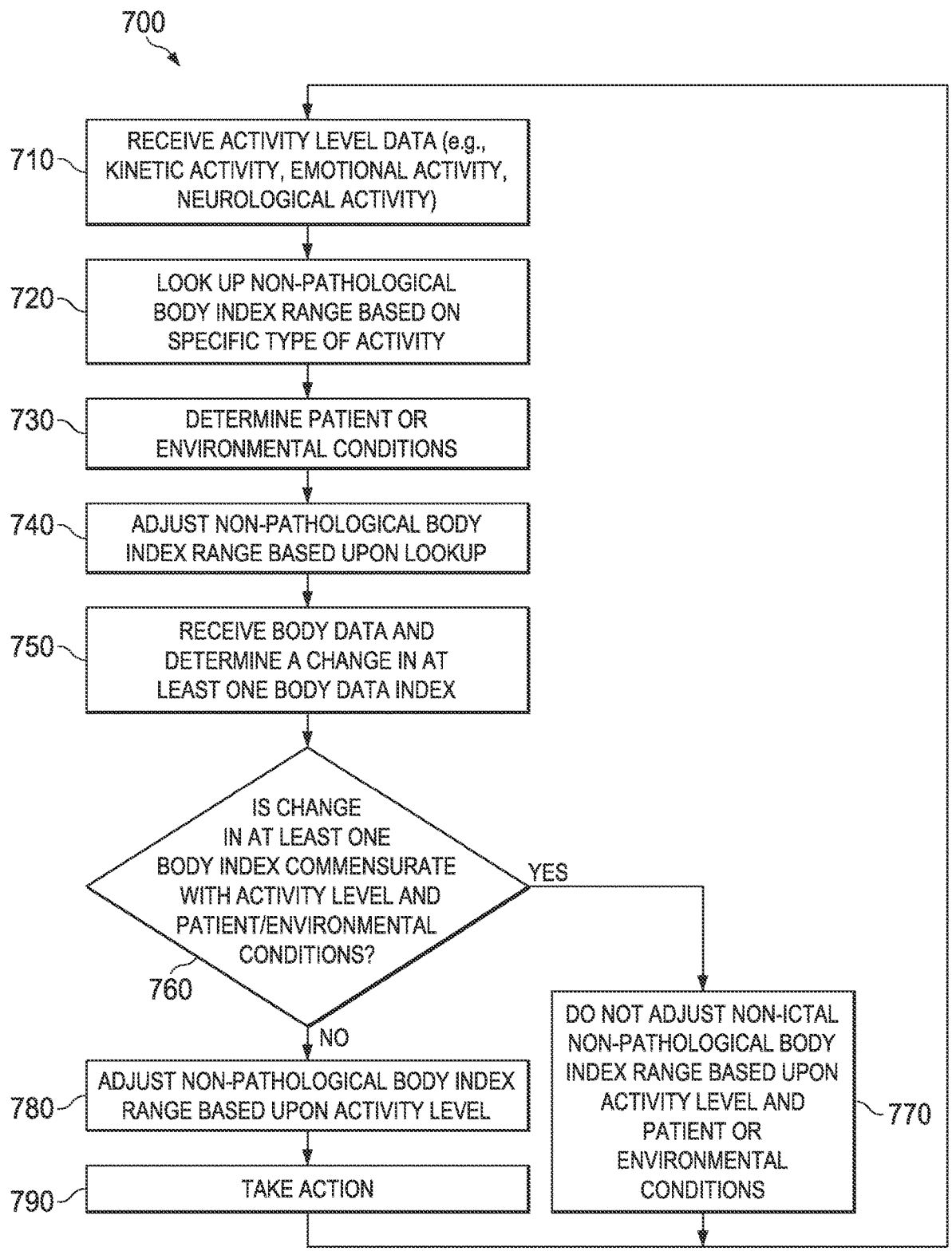
FIG. 7 shows a flowchart representation of a method, according to some embodiments of the present disclosure.

FIG. 7 shows a flowchart representation of a method 700 of dynamically adjusting a non-pathological range for at least one body index range according to one embodiment of the invention. The non-pathological range for the at least one body index may be based upon work level data and patient or environmental conditions, according to some embodiments. First, patient activity data may be received at 710. This received data may be related to the origin(s), type, or magnitude of the activity, i.e., may provide a qualitative, semi-quantitative, or quantitative measure of the kinetic, emotional, and/or cognitive contributions to the patient's activity level. A non-pathological range (e.g., a non-ictal heart rate range) for the at least one body index may be determined at 720, based on the patient's activity. In some embodiments of the invention, the non-pathological range for the at least one body index may be adjusted in view of at least one patient or environmental condition. In such cases, patient or environmental condition data may be received at 730. The activity-based non-pathological range for the at least one body index from 720 may then be adjusted at 740 (e.g., based on a lookup table or calculations). The magnitude of the adjustment to the activity-based range may depend upon the sensitivity of the particular body index to the patient or environmental factor(s) being considered. Body data of the patient may be received, and a change in the at least one body index may be determined, at 750.

From the non-pathological body index range(s) and the at least one body index corresponding thereto, it may be determined at 760 whether the change in the at least one body index is commensurate with the patient's activity level or type, and (in some embodiments) the at least one patient or environmental condition(s). If the change is commensurate with the activity level and conditions, then the non-pathological body index range (e.g., a non-ictal heart rate range) is not adjusted at 770 based on activity level or the patient or environmental condition(s), and flow returns to 710. If the change is not commensurate with the patient's activity level or type, or with patient/environmental condition(s), then the non-pathological body index range (e.g., a non-ictal heart rate range) is adjusted at 780 based on activity level, and an action is taken at 790.

It should be noted that, in some embodiments, adjustments at 740 of the non-pathological body index range may be required only in situations where pathological and non-pathological values of the body signal overlap.

Figure 8:
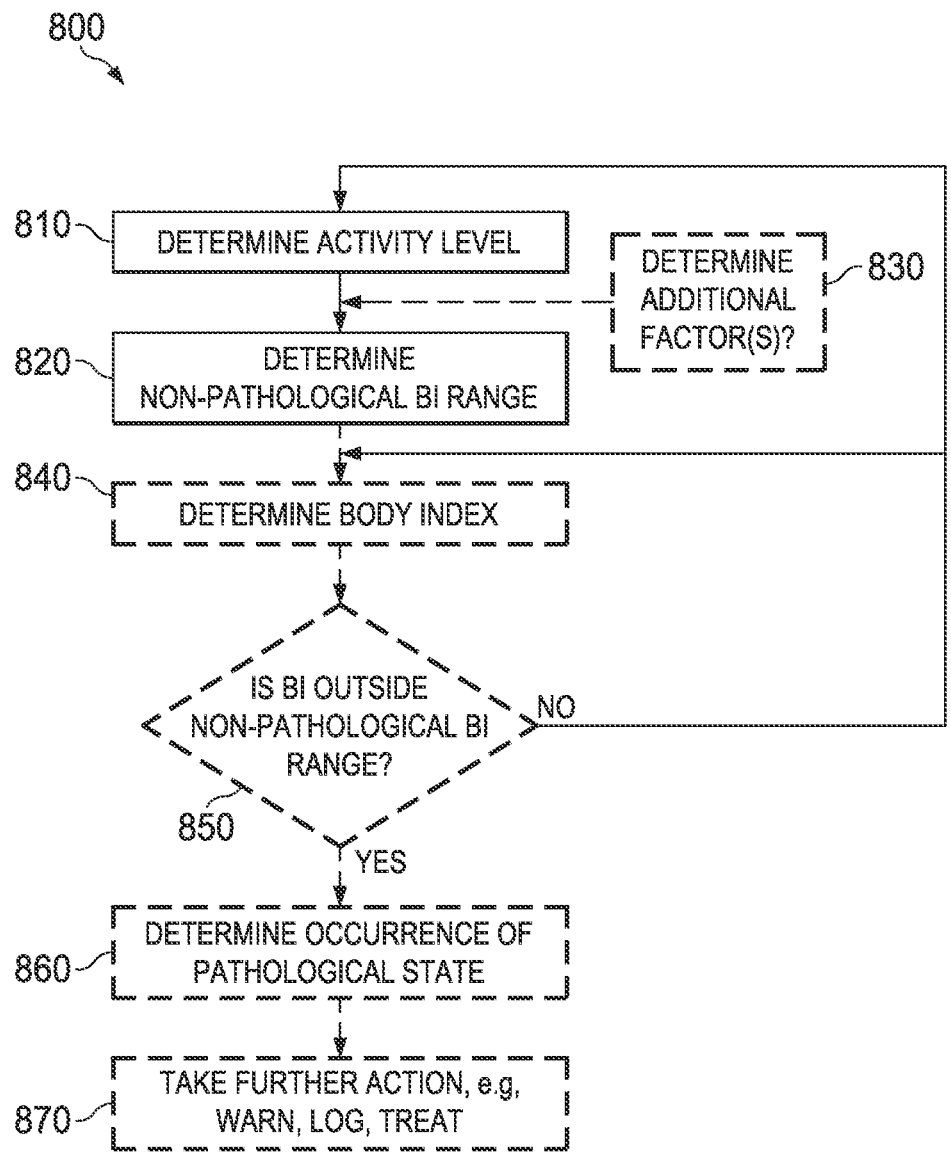
FIG. 8 shows a flowchart representation of a method, according to some embodiments of the present disclosure.

FIG. 8 shows a flowchart representation of a method 800 of determining if the patient is in a pathological or a non-pathological state. First, an activity level of the patient may be determined at 810, and a non-pathological body index range may be determined at 820, based at least in part on the activity level. In some embodiments, one or more additional factors may be determined at 830 and the non-pathological body index (BI) range may be determined at 820, based at least in part on the additional factor(s) and/or the activity level. Examples of such additional factors include, but are not limited to, those described supra.

After the non-pathological body index range is determined at 820, a body index value of the patient may be determined at 840. In some embodiments, multiple body indices may be determined, to increase the specificity and sensitivity of distinguishing between pathological and non-pathological states. If the body index value is determined at 850 to be outside the non-pathological body index range, then it may be determined at 860 that a pathological state of the patient has occurred. Thereafter, a further action, such as warning, treating, or logging the occurrence and/or the severity of the pathological state, may be taken at 870. If the body index value is found at 850 to be within the non-pathological body index range, then flow may return to any of determining the body index value at 840, determining the non-pathological body index range at 820, or determining the activity level at 810.

Figure 9:
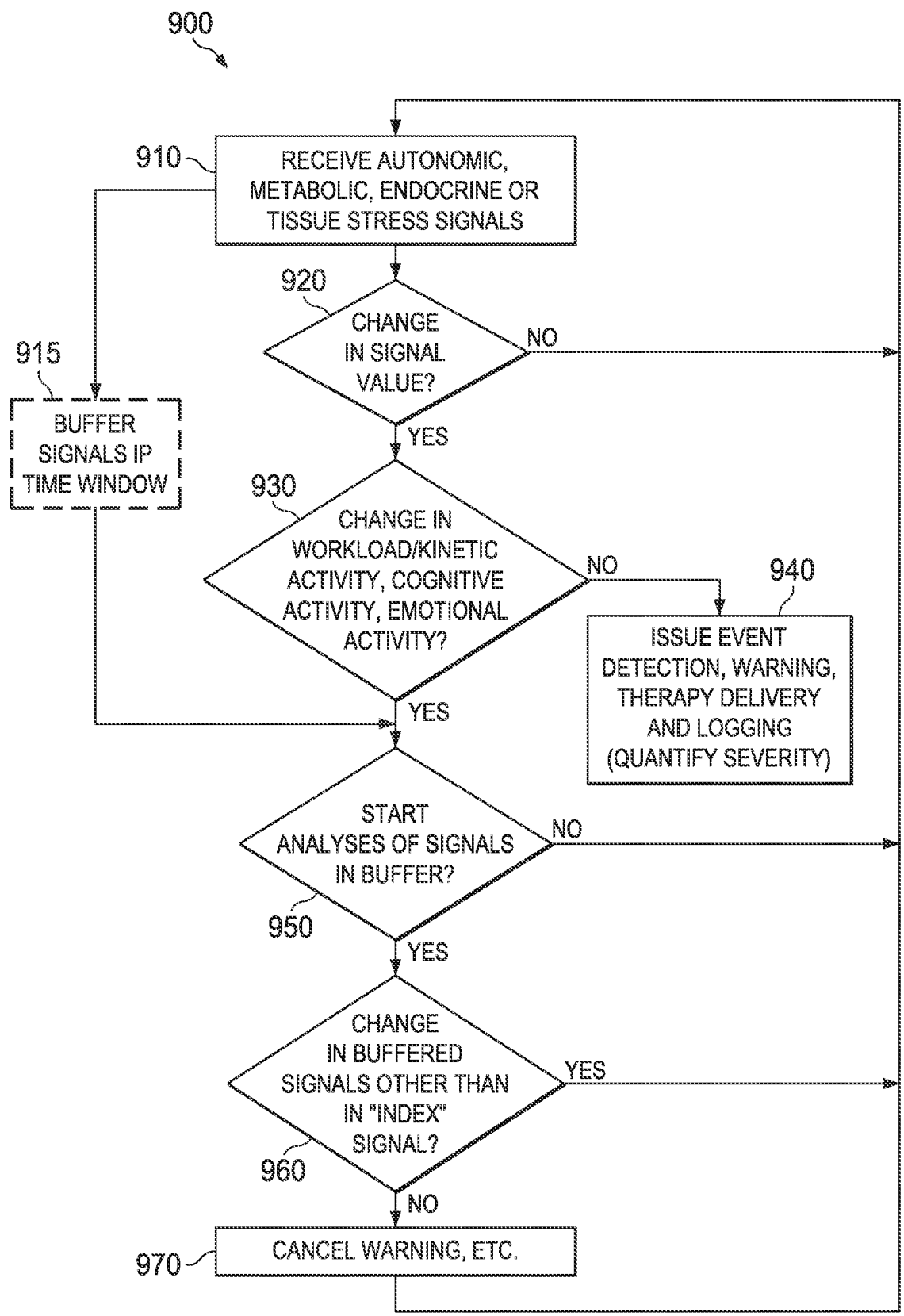
FIG. 9 shows a flowchart representation of a method, according to some embodiments of the present disclosure.

FIG. 9 shows a flowchart representation of a method 900, according to some embodiments of the present disclosure. One or more body signals, such as autonomic, metabolic, endocrine, or tissue stress signals, may be received at 910 and, in some embodiments, the body signals from a first time window may be buffered at 915. The body signals buffered at 915 may be the same or different from the first body signal referred to below.

A determination is made at 920 whether the value of the first body signal has changed. If the body signal is unchanged (i.e., is the same or has only insubstantial differences to prior value(s)), then flow returns to receiving at 910. If the body signal has changed, it is then determined at 930 whether a change in the patient's activity level, e.g., work load, kinetic activity, cognitive activity, or emotional activity has occurred.

If the determination at 930 is that the patient's activity level is unchanged, then one or more actions may be taken at 940, such as issuing a pathological state (e.g., an epileptic seizure) detection, issuing a warning of the pathological state, delivering a therapy for the pathological state to the patient, or logging the pathological state or the severity thereof. If the patient's activity level has changed, then analysis of the body signals, if any, buffered at 915 may begin (element 950).

The analysis at 950 may indicate whether there is a change in one or more buffered body signals other than the first body signal. If it is determined at 960 that no change has occurred in other body signals that should change with the pathological state, then any previously taken action, such as issuing a pathological state detection, issuing a warning of the pathological state, delivering a therapy for the pathological state to the patient, or logging the pathological state or the severity thereof, may have been taken in error. In light thereof, the detection, the warning, etc., may be canceled, etc. at 970 and this information logged for future reference.

Figure 10:
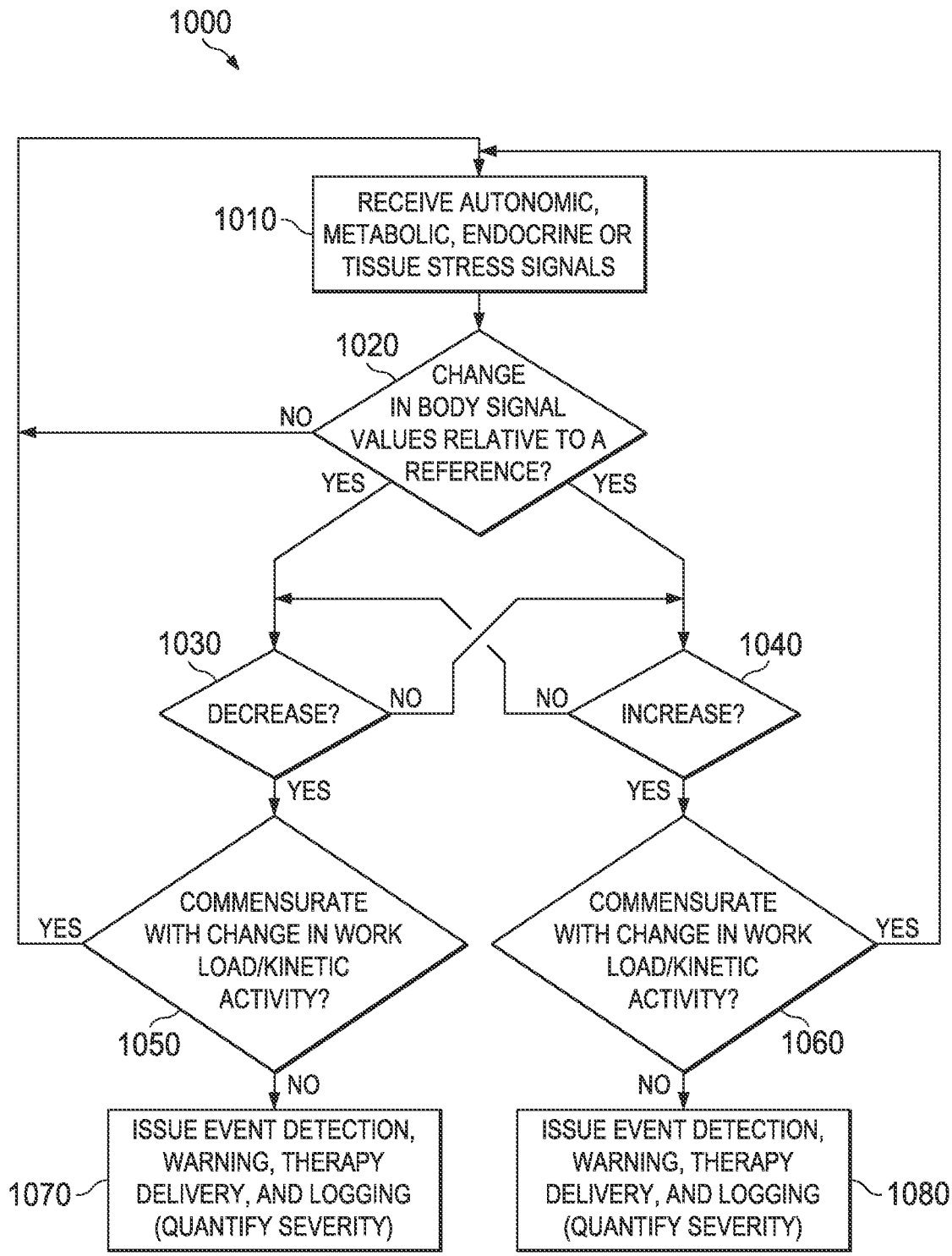
FIG. 10 shows a flowchart representation of a method, according to some embodiments of the present disclosure.

FIG. 10 shows a flowchart representation of a method 1000, according to some embodiments of the present disclosure. One or more body signals, such as autonomic, metabolic, endocrine, or tissue stress signals, may be received at 1010. A determination may be made at 1020 whether the value of a first body signal has changed. If said body signal is unchanged (i.e., is the same or has only insubstantial differences to prior value(s)), then flow returns to receiving at 1010.

If the value of the first body signal has changed, then it may be determined whether the value has decreased (at 1030) or increased (at 1040). If both element 1030 and element 1040 indicate the value has neither decreased nor increased, then flow may return to receiving at 1010. If one or the other of elements 1040 and 1030 indicate the value has increased or decreased, then a determination may be made at 1050 or 1060 whether the increase or decrease is commensurate with the patient's activity level or a change thereof.

From either determination at 1050 or 1060, if the change is commensurate with the patient's activity level and/or a change in activity level, then flow may return to receiving at 1010. If the change is not commensurate with the patient's activity level or change in activity level, then one or more actions may be taken at 1070 or 1080, such as issuing a pathological state (e.g., an epileptic seizure) detection, issuing a warning of the pathological state, delivering a therapy for the pathological state to the patient, or logging the pathological state or the severity thereof. It may be the case that a pathological state detected at 1070 (arising from a body signal value decrease not commensurate with a change in the patient's activity level or a change thereof) may be different from one detected at 1080. In other words, decreases or increases in one or more of autonomic, metabolic, endocrine, or tissue stress signal values may be greater or lesser than expected from the patient's activity level, and a granularity of outputs between elements 1070 and 1080 may exist.

Figure 11:
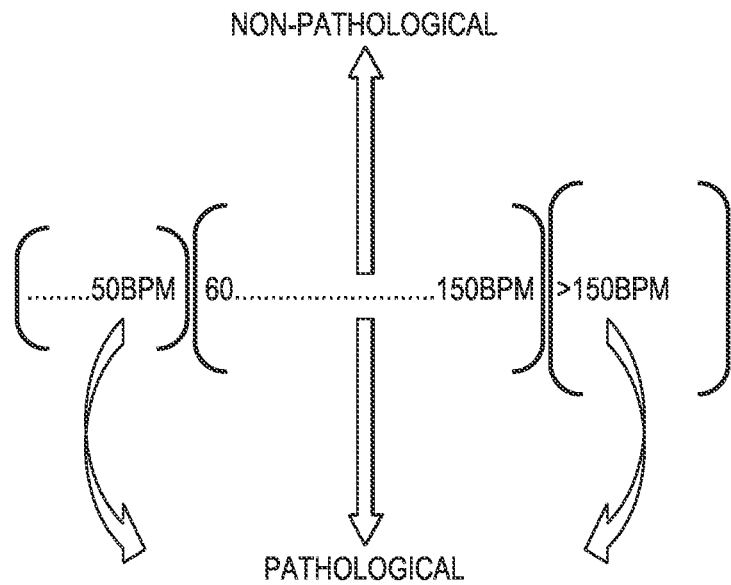
FIG. 11 shows a conceptual depiction of pathological and non-pathological body data (e.g., heart rate) value ranges, according to some embodiments of the present disclosure.

FIG. 11 shows a conceptual depiction of pathological and non-pathological body data (e.g., heart rate) value ranges. Certain heart rate ranges, such as below 50 bpm and above 150 bpm, are essentially always pathological when seen in patients having normal levels of physical fitness and either resting or engaged in mild activity (e.g., walking) Intermediate heart rate ranges, such as from 50-150 bpm, may be pathological, or may be non-pathological, depending on the kinetic and/or emotional/cognitive activity levels of the patient. In other words, heart rate values that are non-pathological or physiologic for certain activity levels may be indicative of a pathological change (e.g. a seizure) for other activity levels.

Figure 12:
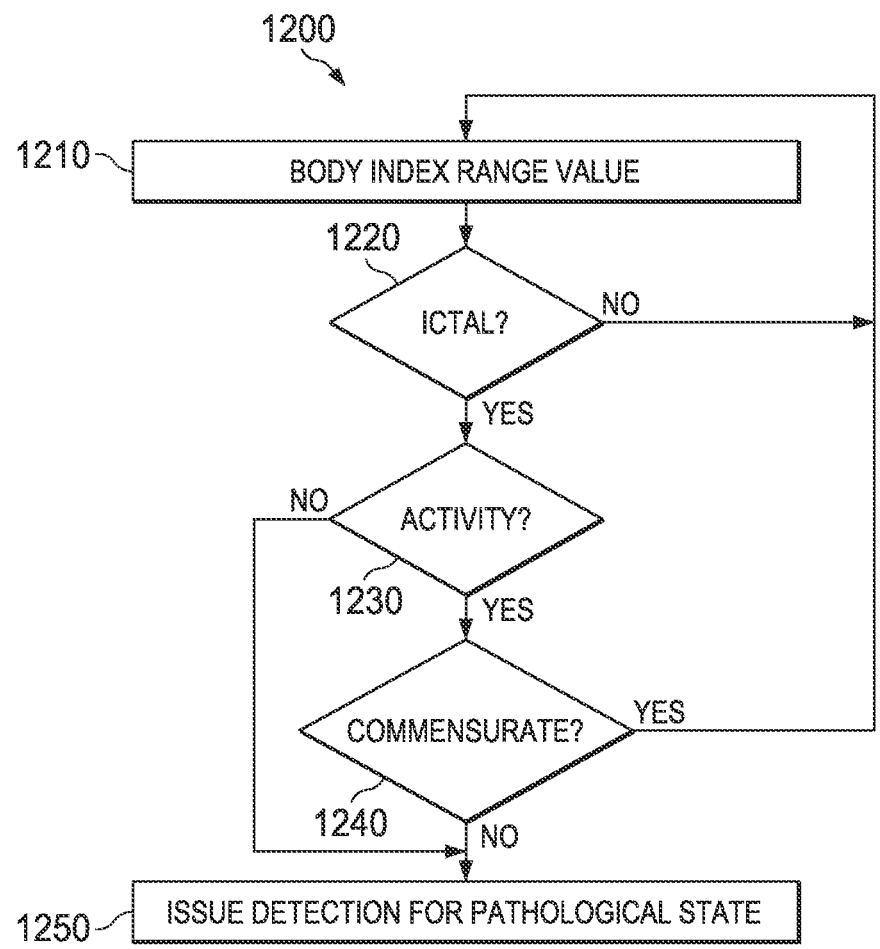
FIG. 12 shows a flowchart representation of a method, according to some embodiments of the present disclosure.

FIG. 12 shows a flowchart representation of a method 1200, according to some embodiments of the present disclosure. A body index range value is determined from patient data at 1210. If the body index range value is found not to be ictal at 1220, flow returns to 1210. If the body index range value is found to be ictal at 1220, a determination is made at 1230 whether the patient is undergoing activity. If the patient is not undergoing activity, the ictal body index range value is indicative of a pathological state (e.g., a seizure), and a detection of the pathological state may be issued at 1250. If the patient is undergoing activity, a determination may be made at 1240 whether the level of the activity is commensurate with the activity. If it is not, then a detection of the pathological state may be issued at 1250. If it is, then flow returns to 1210.

The methods depicted in FIGS. 6-10 and 12 and described above may be governed by instructions that are stored in a non-transitory computer readable storage medium and that are executed by, e.g., a processor 217 of the medical device 200. Each of the operations shown in FIG. 6-10 may correspond to instructions stored in a non-transitory computer memory or computer readable storage medium. In various embodiments, the non-transitory computer readable storage medium includes a magnetic or optical disk storage device, solid state storage devices such as flash memory, or other non-volatile memory device or devices. The computer readable instructions stored on the non-transitory computer readable storage medium may be in source code, assembly language code, object code, or other instruction format that is interpreted and/or executable by one or more processors.

In certain embodiments, the present disclosure relates to a detection of an undesirable (e.g., pathological) state change thorough the determination of changes (e.g., increases or decreases) in the values of body indices in relation to reference values regardless of whether or not said reference value is pathological or non-pathological but taking into account the work or activity level of the patient and, where applicable, environmental conditions. For example, in the case of a patient with an abnormally elevated heart rate, a decrease in said rate toward or into the normal range may be indicative of a pathological state such as an epileptic seizure that reduces heart rate.

In some embodiments, the present disclosure relates to the following numbered paragraph:

201. A non-transitory computer readable program storage unit encoded with instructions that, when executed by a computer, perform a method of detecting a pathological body state of a patient, comprising:
  determining an activity level of said patient; and
  determining a non-pathological range for said body index, based at least in part on said activity level.

301. A non-transitory computer readable program storage unit encoded with instructions that, when executed by a computer, perform a method, comprising:
  determining if a body index of a patient is outside a non-pathological range;
  determining if the patient's kinetic activity is commensurate with the body index value;
  indicating the occurrence of a seizure, if the kinetic activity is not commensurate with the body index value.

401. A method for detecting a pathological body state of a patient, comprising:
  receiving a first body signal of the patient;
  determining a change in a first body index, based on said first body signal;
  determining an activity level of said patient;
  determining if said change in said first body index is commensurate with said determined activity level; and,
  taking a further action in response to determining that said change in said first body index is not appropriate/commensurate/expected/normal for said determined activity level.

What is claimed:

1. A method for detecting an epileptic seizure of a patient, comprising:
  receiving by a medical device a first body signal of the patient;
  receiving by the medical device a second body signal of the patient;
  determining by the medical device a first body index from the first body signal;
  determining by the medical device a second body index from the second body signal;
  determining by the medical device an activity level of the patient based on sensed data from one or more sensors selected from a group consisting of one or more kinetic sensors, one or more muscle temperature sensors, one or more oxygen measuring devices, one or more lactic acid accumulation sensors, one or more sweat sensors, or one or more neurogram sensors;
  determining by the medical device a first non-pathological range for the first body index based on the activity level of the patient via a work level look-up table where the work level look-up table contains information relating the first non-pathological body index range to the activity level of the patient where the first non-pathological range has a first lower limit value or a first number and a first upper limit value or a second number;
  determining by the medical device a second non-pathological range for the second body index based on the activity level of the patient via the work level look-up table where the work level look-up table contains information relating the second non-pathological body index range to the activity level of the patient where the second non-pathological range has a second lower limit value or a third number and a second upper limit value or a fourth number, the third number being different than the first number and the fourth number being different than the second number;
  comparing by the medical device the first body index to the first non-pathological range for the first body index;

comparing by the medical device the second body index to the second non-pathological range for the second body index; and detecting by the medical device the epileptic seizure when the first body index reaches a first value that is outside the first non-pathological range for the first body index and the second body index reaches a second value that is outside the second non-pathological range for the second body index; and initiating one or more therapeutic actions based on a detection of the epileptic seizure.

2. The method of claim 1, wherein the first body signal and the second body signal are the same body signal.

3. The method of claim 2, wherein the first body signal is a cardiac signal and the second body signal is a respiratory signal.

4. The method of claim 1, further comprising:
in response to detecting the epileptic seizure, performing by the medical device at least one further action selected from issuing a notice of an epileptic seizure detection, delivering a therapy, issuing a warning, logging a time and a date of occurrence of the epileptic seizure detection, logging a response to the therapy, and logging a severity of the epileptic seizure.

5. The method of claim 1, wherein the first body index is selected from a heart rate, a heart rate rhythm, a heart rate variability, a blood pressure, and the second body index is selected from one of a respiratory rate, a respiratory rhythm, an end-tidal $CO_2$, a cognitive activity, a dermal activity, an arterial pH, a cortisol level, a catecholamine level, or a blood oxygen saturation.

6. The method of claim 1, wherein determining by the medical device the first non-pathological range for the first body index and the second non-pathological range for the second body index are further based at least in part on one or more of a time of day, an environmental condition, a patient's body weight and height, a patient's body mass index, a patient's gender, a patient's age, an indicator of a patient's overall health, or an indicator of a patient's overall fitness.

7. The method of claim 1, wherein the first activity level is an activity level for a time window.

8. The method of claim 1, wherein determining by the medical device the first activity level occurs in real time.

9. The method of claim 1, further comprising repeating by the medical device the steps of determining the first activity level of the patient and determining the first non-pathological range for the first body index at a time interval ranging from about 100 times per second to about once every four hours.

10. The method of claim 1, wherein determining by the medical device the first non-pathological range for the first body index comprises determining the first non-pathological range for the first body index for a first time point based on a patient's activity in a first time window and determining by the medical device the second non-pathological range for the second body index comprises determining the second non-pathological range for the second body index for the first time point based on the patient's activity in a second time window.

11. The method of claim 10, wherein a duration of the first time window is from 1 second to 2 hours and a duration of the second time window is from 1 second to 2 hours.

12. The method of claim 1, wherein determining by the medical device the first body index from the first body signal comprises determining a change in the first body index, and wherein detecting the epileptic seizure when the first body index reaches the first value that is outside the first non-pathological range comprises determining if the change in the first body index is commensurate with the first activity level.

13. The method of claim 10, wherein a first window duration for the first body index is different from a second window duration for the second body index.

14. The method of claim 1, wherein the one or more kinetic sensors are an accelerometer, an inclinometer, an electromyography (EMG) sensor, a neurogram sensor, a force transducer, or an ergometer.

15. A method of determining an epileptic seizure in a patient, comprising:
receiving by a medical device data relating to an activity level of the patient, wherein the data is received from a lactic acid accumulation sensor;
determining by the medical device the activity level of the patient based on the data relating to the activity level;
receiving by the medical device at least one body signal of the patient;
determining by the medical device at least a first body index based on the at least one body signal;
dynamically determining by the medical device a reference value range for the at least the first body index based on the activity level;
determining by the medical device that the patient is in one of a non-pathological state or an epileptic seizure state, wherein the patient is determined to be in the non-pathological state if the at least the first body index is within the reference value range for the activity level where the reference value range starts at a first number or a lower limit and ends at a second number or an upper limit, and the patient is determined to be in the epileptic seizure state if the at least the first body index reaches a value that is outside an activity level reference value range; and
taking at least one further action by the medical device based on determining that the patient is in the epileptic seizure state, wherein the further action is treating the epileptic seizure state.

16. The method of claim 15, wherein the reference value range comprises one of a non-pathological range and a pathological range for a given activity level.

17. The method of claim 15, wherein the at least one body signal is selected from a cardiac signal, a respiratory signal, a blood signal, a dermal signal and an endocrine signal.

18. The method of claim 15, wherein the first body index is selected from:
a cardiac index based on a cardiac signal, wherein the cardiac index is selected from a heart rate, a heart rhythm, a heart rate variability, and a blood pressure;
a respiratory index based on a respiratory signal, wherein the respiratory index is selected from a respiratory rate, a respiratory rhythm, a blood oxygen saturation, and an end tidal $CO_2$ concentration;
a dermal index based on a dermal signal, wherein the dermal index is selected from a skin resistivity and a skin conductivity;
a blood index based on a blood signal, wherein the blood index is selected from an arterial pH and a lactic acid concentration; and
an endocrine index based on a endocrine signal, wherein the endocrine signal is selected from a cortisol level and a catecholamine level.

19. The method of claim 15, wherein the value for a pathological range is a first value outside a normal range for a given activity level.

20. The method of claim 15, wherein the further action includes at least one of issuing a warning to the patient or a caregiver regarding the epileptic seizure state, logging the occurrence of the epileptic seizure, logging the response to a therapy, or logging a severity of the epileptic seizure.

21. A medical device system, comprising:
- at least one kinetic sensor configured to collect at least one kinetic signal from a patient;
- an activity level circuit configured to determine an activity level of the patient, based on at least one of the one kinetic signal and a muscle force signal;
- at least one sensor configured to sense a non-kinetic signal and a non-muscle body signal;
- a body index determination circuit configured to determine at least a first body index based on the body signal;
- a body index range circuit, configured to determine a non-pathological body index range for the at least a first body index via a work level look-up table where the work level look-up table contains information relating the non-pathological body index range to the activity level of the patient; and
- a pathological state determination circuit, configured to determine that the patient is in one of a non-pathological state or an epileptic seizure state, wherein the patient is determined to be in the non-pathological state if the at least the first body index is within the non-pathological body index range for the at least the first body index, and the patient is determined to be in the epileptic seizure state if the at least the first body index reaches a value that is outside the non-pathological body index range for the at least the first body index; and
- a treatment unit configured to initiate one or more therapeutic actions based on a detection of the epileptic seizure state;
- wherein the body signal is selected from a heart rhythm, a heart rate variability, a blood pressure, a respiratory rate, a respiratory rhythm, an end tidal $CO_2$, a dermal activity, an arterial pH, a cortisol level, a catecholamine level, or a blood oxygen saturation.

22. The medical device system of claim 21, further comprising an additional factor circuit configured to determine one or more of a time of day, an environmental temperature and an environmental humidity, an indicator of a patient's overall health, an indicator of a patient's overall fitness, or an indicator of a patient's level of consciousness, and provide an output relating to the determination;
- wherein the body index range circuit is further configured to determine a non-pathological body index range for the at least the first body index based at least in part on the output of the additional factor circuit.

* * * * *